(12) United States Patent
Verhulst et al.

(10) Patent No.: US 7,993,376 B2
(45) Date of Patent: Aug. 9, 2011

(54) METHODS OF IMPLANTING A MOTION SEGMENT REPAIR SYSTEM

(75) Inventors: Dominique Verhulst, Schilde (BE); Amie Borgstrom, Stanford, CA (US); Charles M. Bartish, Jr., Providence, RI (US); John Riley Hawkins, Cumberland, RI (US); SeungKyu Daniel Kwak, Grafton, MA (US); William Dunbar, Bethlehem, CT (US); Katherine Torres, Westport, MA (US)

(73) Assignee: DePuy Spine, Inc., Raynham, MA (US)

( * ) Notice: Subject to any disclaimer, the term of this patent is extended or adjusted under 35 U.S.C. 154(b) by 872 days.

(21) Appl. No.: 11/164,643

(22) Filed: Nov. 30, 2005

(65) Prior Publication Data

US 2007/0073405 A1    Mar. 29, 2007

Related U.S. Application Data

(60) Provisional application No. 60/721,603, filed on Sep. 29, 2005.

(51) Int. Cl.
*A61B 17/88* (2006.01)
(52) U.S. Cl. ........................................ 606/279
(58) Field of Classification Search .... 623/17.11–17.16; 606/279
See application file for complete search history.

(56) References Cited

U.S. PATENT DOCUMENTS

| | | | |
|---|---|---|---|
| 4,743,260 A | 5/1988 | Burton | |
| 5,092,866 A | 3/1992 | Beard | |
| 5,282,863 A | 2/1994 | Burton | |
| 5,387,213 A | 2/1995 | Breard et al. | |
| 5,415,661 A | 5/1995 | Holmes | |
| 5,474,086 A | 12/1995 | McCormick et al. | |
| 5,540,688 A | 7/1996 | Navas | |
| 5,556,431 A | 9/1996 | Buttner-Janz | |
| 5,562,737 A | 10/1996 | Graf | |
| 5,571,191 A | 11/1996 | Fitz | |
| 5,672,175 A | 9/1997 | Martin | |
| RE36,221 E | 6/1999 | Breard et al. | |
| 5,961,516 A | 10/1999 | Graf | |
| 5,964,761 A * | 10/1999 | Kambin | 606/304 |
| RE36,758 E | 6/2000 | Fitz | |
| 6,110,210 A * | 8/2000 | Norton et al. | 623/17.16 |
| 6,132,464 A | 10/2000 | Martin | |
| 6,267,764 B1 | 7/2001 | Elberg | |
| 6,273,888 B1 | 8/2001 | Justis | |
| 6,277,120 B1 * | 8/2001 | Lawson | 606/263 |
| 6,283,966 B1 * | 9/2001 | Houfburg | 606/914 |

(Continued)

FOREIGN PATENT DOCUMENTS

EP        0669109        2/1994

(Continued)

*Primary Examiner* — Thomas C Barrett
*Assistant Examiner* — Sameh Boles
(74) *Attorney, Agent, or Firm* — Nutter McClennen & Fish LLP

(57) ABSTRACT

Various methods and devices are provided for implanting a motion segment repair system. In particular, exemplary methods and devices are provided for implanting a spinal disc implant and/or a PDS device using a posterior surgical approach, including methods and devices for distracting adjacent vertebrae using a posterior surgical approach, methods and devices for posteriorly introducing a spinal implant into a disc space between adjacent vertebrae, and methods and devices for coupling a PDS device to the adjacent vertebrae to provide a complete motion segment repair system that is implanted using a posterior surgical approach.

21 Claims, 13 Drawing Sheets

U.S. PATENT DOCUMENTS

| | | | |
|---|---|---|---|
| 6,371,986 B1 * | 4/2002 | Bagby | 623/17.11 |
| 6,419,703 B1 | 7/2002 | Fallin | |
| 6,554,831 B1 | 4/2003 | Rivard et al. | |
| 6,565,605 B2 | 5/2003 | Goble | |
| 6,579,319 B2 | 6/2003 | Goble | |
| 6,610,091 B1 | 8/2003 | Reiley | |
| 6,645,207 B2 | 11/2003 | Dixon | |
| 6,669,729 B2 | 12/2003 | Chin | |
| 6,811,567 B2 | 11/2004 | Reiley | |
| 7,060,100 B2 * | 6/2006 | Ferree et al. | 623/17.16 |
| 2002/0065557 A1 | 5/2002 | Goble et al. | |
| 2002/0072800 A1 | 6/2002 | Goble et al. | |
| 2002/0123806 A1 | 9/2002 | Reiley | |
| 2002/0133155 A1 | 9/2002 | Ferree | |
| 2003/0004572 A1 | 1/2003 | Goble et al. | |
| 2003/0009227 A1 * | 1/2003 | Lambrecht et al. | 623/17.16 |
| 2003/0028250 A1 | 2/2003 | Reiley et al. | |
| 2003/0055427 A1 | 3/2003 | Graf | |
| 2003/0083657 A1 | 5/2003 | Drewry | |
| 2003/0109880 A1 | 6/2003 | Shirado et al. | |
| 2003/0135277 A1 | 7/2003 | Bryan et al. | |
| 2003/0153912 A1 | 8/2003 | Graf | |
| 2003/0171749 A1 | 9/2003 | Le Couedic et al. | |
| 2003/0171750 A1 | 9/2003 | Chin | |
| 2003/0191470 A1 | 10/2003 | Ritland | |
| 2003/0191532 A1 | 10/2003 | Goble et al. | |
| 2003/0220642 A1 | 11/2003 | Freudiger | |
| 2003/0220643 A1 | 11/2003 | Ferree | |
| 2004/0002708 A1 | 1/2004 | Ritland | |
| 2004/0006391 A1 | 1/2004 | Reiley | |
| 2004/0049189 A1 | 3/2004 | Le Couedic et al. | |
| 2004/0049190 A1 | 3/2004 | Biedermann et al. | |
| 2004/0049272 A1 | 3/2004 | Reiley | |
| 2004/0049273 A1 | 3/2004 | Reiley | |
| 2004/0049274 A1 | 3/2004 | Reiley | |
| 2004/0049275 A1 | 3/2004 | Reiley | |
| 2004/0049276 A1 | 3/2004 | Reiley | |
| 2004/0049277 A1 | 3/2004 | Reiley | |
| 2004/0049278 A1 | 3/2004 | Reiley | |
| 2004/0049281 A1 | 3/2004 | Reiley | |
| 2004/0073215 A1 | 4/2004 | Carli | |
| 2004/0106999 A1 | 6/2004 | Mathews | |
| 2004/0111154 A1 | 6/2004 | Reiley | |
| 2004/0116927 A1 | 6/2004 | Graf | |
| 2004/0127903 A1 * | 7/2004 | Schlapfer et al. | 606/69 |
| 2004/0143264 A1 | 7/2004 | McAfee | |
| 2004/0186475 A1 | 9/2004 | Falahee | |
| 2004/0236329 A1 | 11/2004 | Panjabi | |
| 2005/0033431 A1 | 2/2005 | Gordon et al. | |
| 2005/0033432 A1 | 2/2005 | Gordon et al. | |
| 2005/0033439 A1 | 2/2005 | Gordon et al. | |
| 2005/0055096 A1 * | 3/2005 | Serhan et al. | 623/17.11 |
| 2005/0101954 A1 | 5/2005 | Simonson | |
| 2005/0101956 A1 | 5/2005 | Simonson | |
| 2005/0113927 A1 | 5/2005 | Malek | |
| 2005/0125066 A1 * | 6/2005 | McAfee | 623/17.16 |
| 2005/0131405 A1 * | 6/2005 | Molz et al. | 606/61 |
| 2006/0131808 A1 | 6/2006 | Daines | |
| 2006/0149229 A1 | 7/2006 | Kwak et al. | |
| 2006/0149230 A1 | 7/2006 | Kwak et al. | |
| 2006/0178745 A1 | 8/2006 | Bartish et al. | |
| 2006/0178746 A1 | 8/2006 | Bartish et al. | |
| 2006/0271046 A1 | 11/2006 | Kwak et al. | |
| 2006/0282075 A1 | 12/2006 | Labrom et al. | |
| 2006/0282079 A1 | 12/2006 | Labrom et al. | |

FOREIGN PATENT DOCUMENTS

| | | |
|---|---|---|
| WO | WO-01/45576 | 6/2001 |
| WO | WO-02/17803 | 3/2002 |
| WO | WO-02/43603 | 6/2002 |
| WO | WO-02/102259 | 12/2002 |
| WO | WO-03/007828 | 1/2003 |
| WO | WO-03/009737 | 2/2003 |
| WO | WO-2004/024011 | 3/2004 |
| WO | WO-2004/034916 | 4/2004 |

* cited by examiner

METHODS OF IMPLANTING A MOTION SEGMENT REPAIR SYSTEM

CROSS REFERENCE TO RELATED APPLICATIONS

The present application claims priority to U.S. Provisional Application No. 60/721,603, filed Sep. 29, 2005 and entitled "Motion Segment Repair System," which is hereby incorporated by reference in its entirety.

BACKGROUND OF THE INVENTION

Disease, advancing age, and trauma can lead to changes in various bones, discs, joints, and ligaments of the body. Some changes and trauma often manifest themselves in the form of damage or degeneration to a spinal disc. This condition often results in chronic back pain, which can be anywhere from mild to severe. This pain can sometimes be eliminated by spinal fusion in which two adjacent vertebral bodies are jointed together after removing the intervening intervertebral disc. A prosthetic device is usually placed between the two adjacent vertebral bodies, in place of the removed disc, to fill the space left by the removed disc and to allow bone to grow between the two vertebral bodies.

More recently, spinal implants, referred to as posterior dynamic stabilizers, have been developed that allow motion between the adjacent vertebrae, thereby restoring normal function to the vertebrae. While these implants have been met with great success, they typically require an anterior surgical approach to be used to position the implant between adjacent vertebrae so as to avoid contact with the spinal cord. The implant sizes and instrumentation also dictate an anterior approach to the spine. Most anterior surgical approaches, however, tend to be invasive due to the nature and amount of the anatomy that needs to be displaced in order to successfully access the disc space. Moreover, the surgical procedure typically requires a general or vascular surgeon to expose the spine, and a spinal surgeon to perform the discectomy and implantation, thereby increasing the costs. Post-operative complications can also occur during an anterior surgical approach, including abdominal wall hematoma, vascular injury, retrograde ejection, and gastrointestinal injury.

Accordingly, there remains a need for improved methods and devices for posterior dynamic stabilization, and in particular for a full motion segment repair system and methods for implanting the same using a posterior or posterior-lateral approach.

BRIEF SUMMARY OF THE INVENTION

The present invention generally provides methods and devices for implanting a motion segment repair system using a posterior or posterio-lateral approach. In one exemplary embodiment, the method can include implanting a disc implant between adjacent superior and inferior vertebrae using a substantially posterior surgical approach and coupling a posterior stabilization device to the adjacent superior and inferior vertebrae. At least one of the disc implant and the posterior stabilization device can have a floating center of rotation to allow the posterior stabilization device to be positioned at various locations relative to the adjacent superior and inferior vertebrae, and to allow and/or control flexion, extension, lateral bending, axial rotation, and/or anterior-posterior shear between the adjacent superior and inferior vertebrae.

In one embodiment, the disc implant can have a floating center of rotation. For example, the disc implant can include first and second end plates with a central core moveably disposed there between. In other embodiments, the disc implant can have a fixed center of rotation. In another embodiment, the posterior stabilization device can have a floating center of rotation. For example, the posterior stabilization can include a first connector that couples to a superior vertebra and a second connector that couples to an adjacent inferior vertebrae. The first and second connectors can be movably mated to one another by a flexible member to allow and/or control flexion, extension, lateral bending, axial rotation, and/or anterior-posterior shear between the adjacent superior and inferior vertebrae. In yet another embodiment, the posterior stabilization device can have a fixed center of rotation. For example, the posterior stabilization device can include a first connector that couples to a superior vertebra and a second connector that couples to an adjacent inferior vertebrae. The first and second connectors can be slidably coupled to one another to allow flexion and extension between the adjacent superior and inferior vertebrae.

In another exemplary method for implanting a motion segment repair system, adjacent superior and inferior vertebrae can be distracted using at least one distraction anchor disposed in a posterior side of each of the adjacent superior and inferior vertebrae. A disc implant can be inserted between the adjacent superior and inferior vertebrae. A bone screw can be implanted over each distraction anchor and a posterior stabilization device can be coupled to the bone screws to couple the adjacent superior and inferior vertebrae to one another. In an exemplary embodiment, first and second distraction anchors can be implanted on opposed lateral sides of the superior vertebra, and third and fourth distraction anchors can be implanted on opposed lateral sides of the inferior vertebra. The adjacent superior and inferior vertebrae can be distracted using a spreading device that engages the distraction anchors. The disc implant is then inserted using a substantially posterior surgical approach.

In another exemplary embodiment, the distraction anchors can be used to re-distribute a load applied to the implant to move the implant in a posterior direction. For example, tension can be applied to a member, e.g., a guidewire, coupled to the disc implant to move the disc implant in a posterior direction while distributing the load along an axis of the distraction anchors. In particular, the member can be coupled to one or more supports extending between the distraction anchors. In an exemplary embodiment, the supports have first and second bores for receiving the distraction anchors, and a third bore for slidably receiving a guidewire therethrough.

Exemplary methods for implanting a disc implant using a posterior approach are also provided. In one embodiment, the method can include introducing a disc implant to an anterior location between adjacent superior and inferior vertebrae using a substantially posterior surgical approach, and pulling the disc implant in a posterior direction to position the disc implant between then adjacent superior and inferior vertebrae. For example, tension can be applied to a guidewire coupled to the disc implant to move the disc implant in a posterior direction. Pulling the disc implant in a posterior direction is effective to distract the adjacent superior and inferior vertebrae. The method can further include coupling a posterior stabilization device to the adjacent superior and inferior vertebrae. In another embodiment, the disc implant can be introduced between the adjacent superior and inferior vertebrae using a guide device. The guide device can be positioned on a posterio-lateral side of a spinal column to guide the disc implant medially between adjacent superior and inferior vertebrae. For example, the disc implant can be moved along a curved pathway formed on the guide device to position the disc implant between the adjacent superior and inferior vertebrae. The guide device can optionally include a pivoting member formed thereon to position the implant between the adjacent superior and inferior vertebrae and to pivot the implant to position it between the adjacent vertebrae.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for stabilizing the posterior elements of the spine, and more preferably methods and devices are provided for implanting a spinal disc implant and/or a posterior dynamic stabilization (PDS) device using a posterior or posterio-lateral approach. In particular, exemplary methods are provided for distracting adjacent vertebrae using a posterior approach, posteriorly introducing a disc implant, and coupling a PDS device to the adjacent vertebrae to provide a full motion segment repair system. A person skilled in the art will appreciate that the term "posterior approach" as used herein is intended to include both posterior and posterio-lateral approaches.

Disc Implants and PDS Devices

The disc implant and PDS device used with the various methods and devices disclosed herein can have a variety of configurations, and virtually any disc implant and PDS device known in the art can be used. In an exemplary embodiment, however, the disc implant and the PDS device are configured to allow at least some movement between adjacent vertebrae coupled thereto, and more preferably at least one device has a floating center of rotation. In particular, one or more joints on the disc implant or PDS device can be configured to allow movement along a center of rotation that moves and thus is not fixed. The other one of the disc implant and PDS device can likewise have a floating center of rotation, or it can have a fixed center of rotation. The use of a disc implant and PDS device having at least one floating center of rotation allows the PDS device to be implanted at various locations relative to the adjacent vertebrae, whereas a motion segment repair system (i.e., disc implant and PDS device) that does not have at least one floating center of rotation requires precise alignment of the PDS device with the disc implant.

Figure 1:
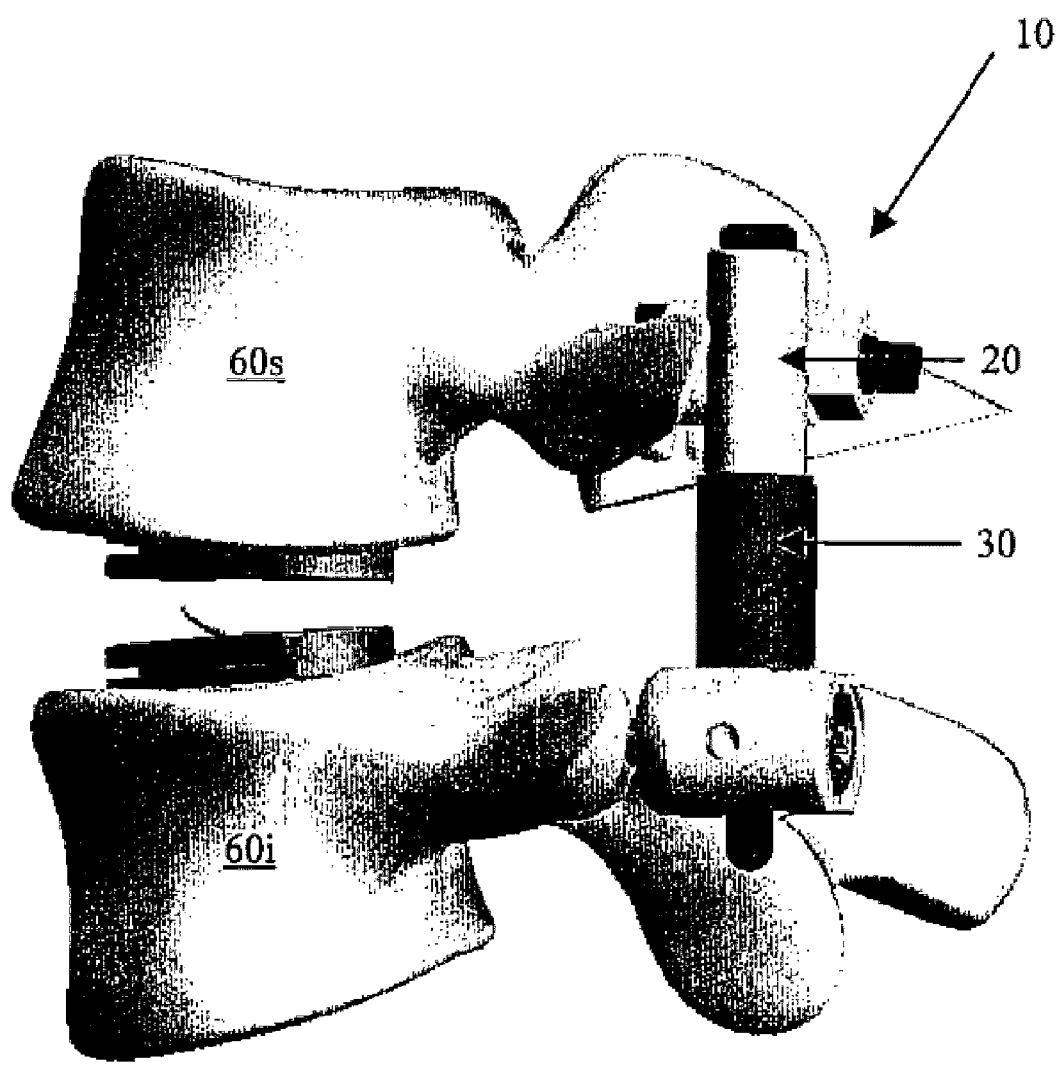
FIG. 1 is a perspective view of a prior art motion segment repair system implanted between two adjacent vertebrae.
Figure 2:
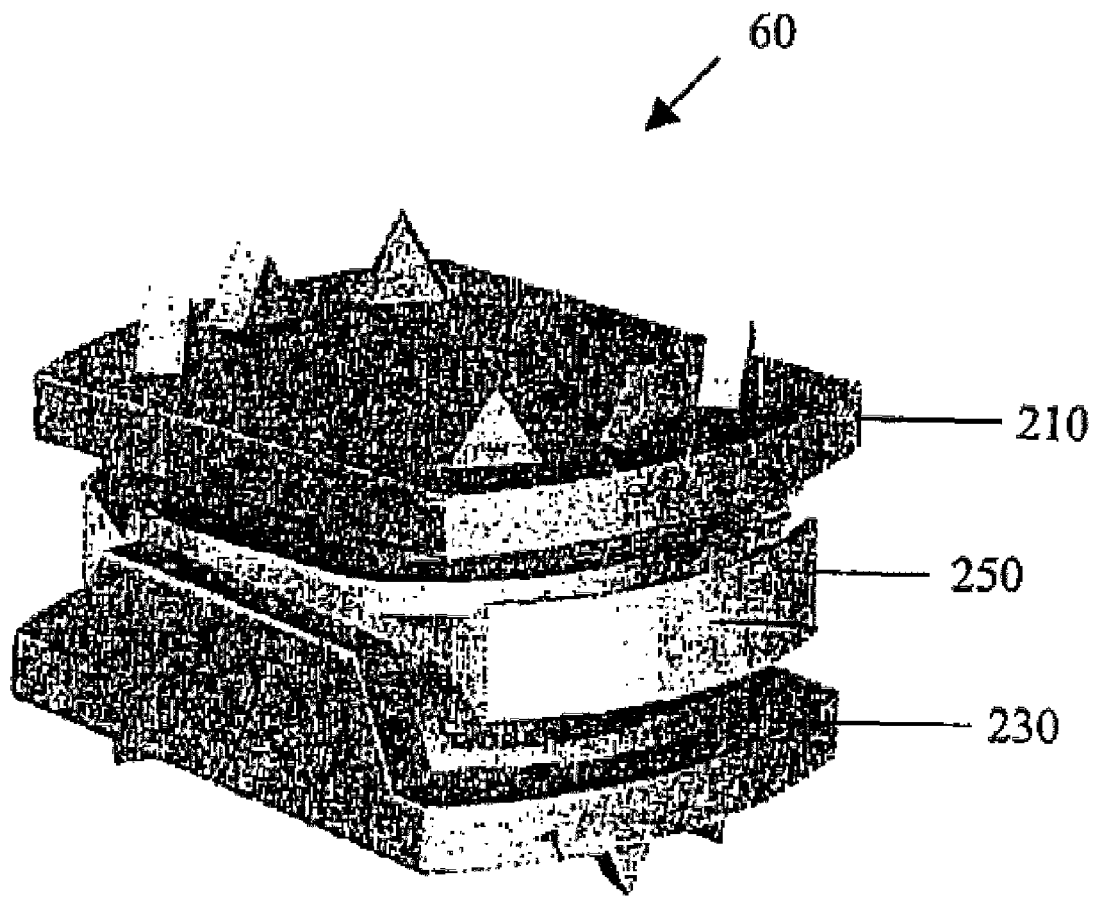
FIG. 2 is a perspective view of a disc implant of the prior art motion segment repair system shown in FIG. 1.
Figure 3:
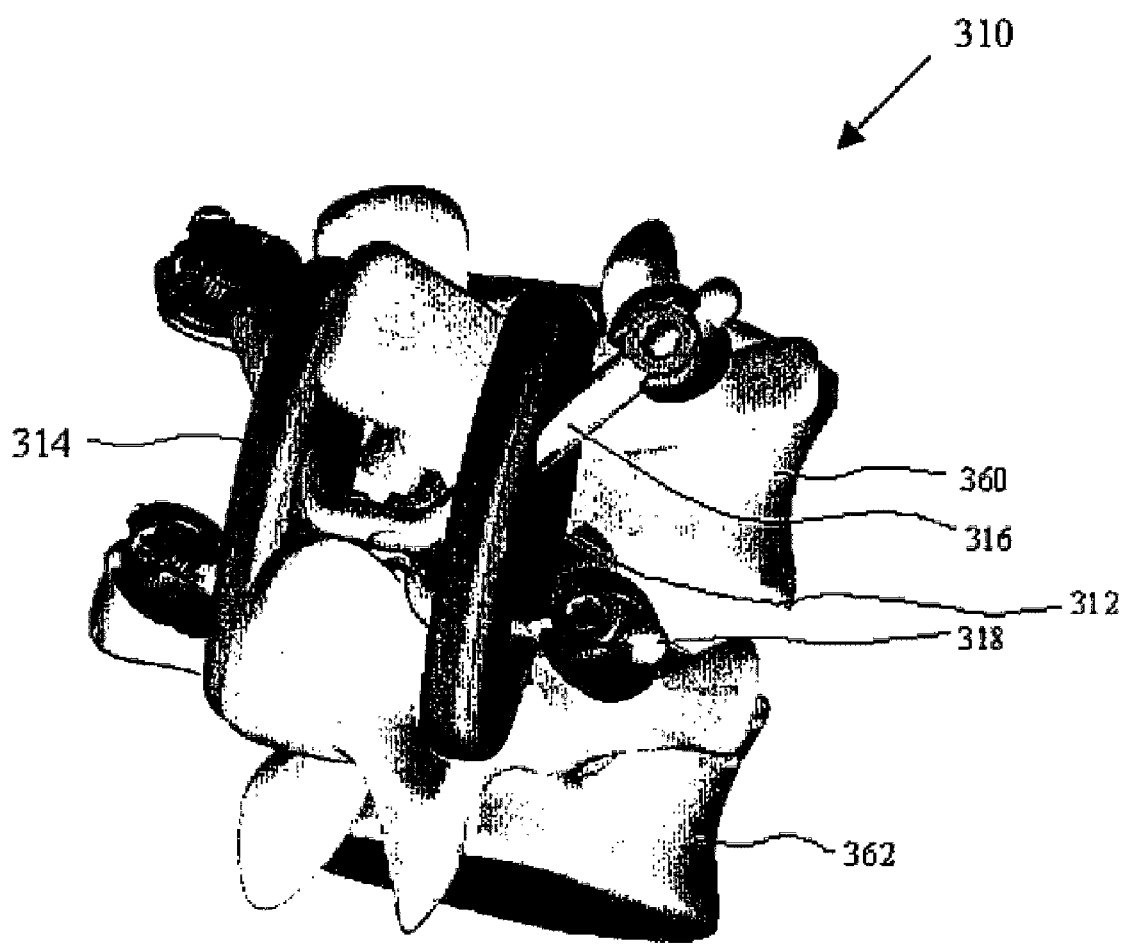
FIG. 3 is a perspective view of one exemplary embodiment of a prior art posterior stabilization device.

FIGS. 1-3 illustrate various exemplary embodiments of a prior art disc implant (FIG. 2) and prior art posterior stabilization devices (FIGS. 1 and 3) that can be used with the various exemplary methods and devices described herein. Referring first to FIG. 1, one exemplary embodiment of a motion segment repair system 10 is shown having a disc implant 60 and a PDS device with a fixed center of rotation. The disc implant 60, which is shown in more detail in FIG. 2, generally includes superior and inferior endplates 210, 230 and a central core 250 disposed therebetween. The superior endplate member 210 is adapted to be positioned adjacent to an endplate of a superior vertebra, and the inferior endplate member 230 is adapted to be positioned adjacent to an endplate of an inferior vertebra. The outer surfaces of the endplate members 210, 230 can be configured to complement the shape of the vertebral endplates. The core 250 can be a resilient member that is adapted to be received between the endplate members 210, 230. As a result, the endplate members 210, 230 can move relative to the core 250 to allow movement of the adjacent vertebrae relative to one another. The implant 60 is described in more detail in U.S. patent application Ser. No. 11/055,025 of DePuy Spine, Inc., filed on Feb. 10, 2005 and entitled "Intervertebral Prosthetic Disc." This application is hereby incorporated by reference in its entirety.

While FIGS. 1-2 illustrate a disc implant having a floating center of rotation, in other embodiments the disc implant can have a fixed center of rotation. Examples of such implants include fixed core implants and ball-and-socket implants.

As previously indicated, FIG. 1 also illustrates one embodiment of a prior art PDS device having a fixed center of rotation. The PDS device generally includes a first member 20 that is coupled to a first vertebra, e.g., the superior vertebra 60s, and a second member 30 that is coupled to a second vertebra, e.g., the inferior vertebra 60i. The first and second members 20, 30 are movably coupled to one another by sliding pins that are slidably disposed through lateral members. In use, the first and second members 20, 30 cooperate to control movement of the superior and inferior vertebrae 60s, 60i relative to one another, and in particular they allow at least some flexion, extension, and lateral bending of the vertebrae 60s, 60i, while substantially restricting posterior-anterior shear and rotation of the vertebrae 60s, 60i. The PDS device is described in more detail in U.S. patent application Ser. No. 10/908,882 filed on May 31, 2005 and entitled "Facet Joint Replacement."Other exemplary embodiments of PDS devices having a fixed center of rotation are also disclosed in U.S. patent application Ser. No. 10/908,882, as well as U.S. patent application Ser. No. 10/905,376 filed on Dec. 30, 2004 and entitled "Posterior Stabilization System." These applications are assigned to DePuy Spine, Inc., and they are hereby incorporated by reference in their entireties.

As indicated above, in other embodiments the PDS device can have a floating center of rotation, i.e. one or more joints on the PDS device can allow movement along a center of rotation that moves and thus is not fixed. FIG. 3 illustrates one embodiment of a prior art PDS device having a floating center of rotation. As shown, the device 310 generally includes first and second flexible members 312, 314, also referred to as dynamic stabilizing elements, and first and second connectors 316, 318, also referred to as stabilizing rods. As shown in FIG. 3B, the device 310 is coupled to superior and inferior vertebrae 360, 362 such that it is effective to perform the function of the posterior elements that connect the vertebrae, or to otherwise control movement of the vertebrae 360, 362. More particularly, the first connector 316, hereinafter referred to as the superior connector 316, is coupled to the superior vertebra 360, and the second connector 318, hereinafter referred to as the inferior connector 318, is coupled to the inferior vertebra 362. The superior and inferior connectors 316, 318 extend through the first and second flexible members 312, 314, such that the connectors 316, 318 are coupled to one another via the flexible members 312, 314. As a result, the connectors 316, 318 and the flexible members 312, 314 are effective to control movement of the vertebrae 360, 362 relative to one another, thereby functioning in place of the posterior elements. In an exemplary embodiment, the flexible members 312, 314 are movable, e.g., rotatable and/or slidable, but preferably not deformable, relative to at least one of the connectors, e.g., the superior connector 316, when the vertebrae 360, 362 are moved within a first range of motion, and at least one of the connectors, e.g., the superior connector 316, is effective to deform, e.g., stretch, rotate, etc., the flexible members 312, 314, or otherwise create resistance, when the superior and inferior vertebrae 360, 362 are moved within a second range of motion beyond the first range of motion. As a result, the PDS device 310 has a floating center of rotation.

Other exemplary embodiments of PDS devices having a floating center of rotation are disclosed in U.S. patent application Ser. No. 11/160,139 filed on Jun. 10, 2005 and entitled "Posterior Dynamic Stabilization X-Device," U.S. patent application Ser. No. 11/160,143 filed on Jun. 10, 2005 and entitled "Posterior Dynamic Stabilization Systems and Methods," U.S. patent application Ser. No. 10/908,882 filed on May 31, 2005 and entitled "Facet Joint Replacement," U.S. patent Ser. No. 10/905,374 filed on Dec. 30, 2004 and entitled "Artificial Facet Joint," and U.S. patent Ser. No. 10/955,207 filed on Sep. 30, 2004 and entitled "Posterior Stabilization Systems And Methods." These applications are all assigned to DePuy Spine, Inc., and they are hereby incorporated by reference in their entireties.

Methods for Implanting Motion Segment Repair Systems

Figure 4:
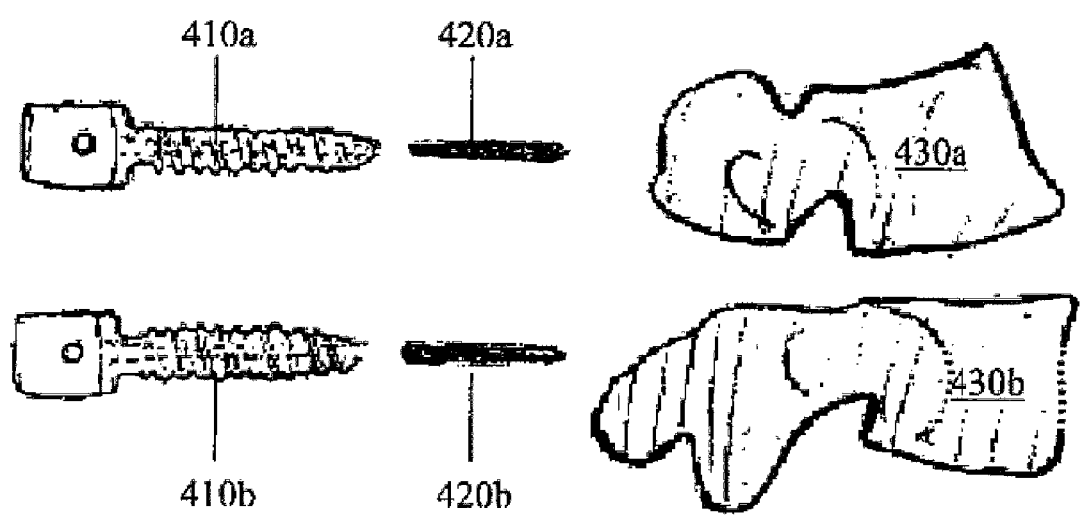
FIG. 4 is a side view of one exemplary method for distracting two adjacent vertebrae using distraction anchors which are configured to receive bone screws there over.
Figure 5A:
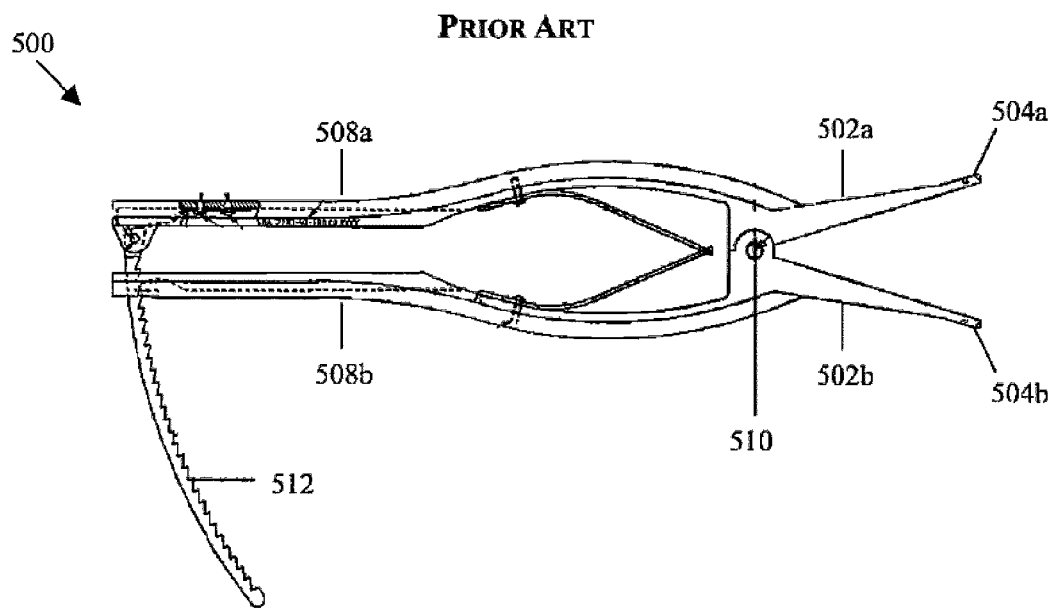
FIG. 5A is a side view of a prior art distraction device that can be used to engage the distraction anchors shown in FIG. 4 to distract the adjacent vertebrae.
Figure 5B:
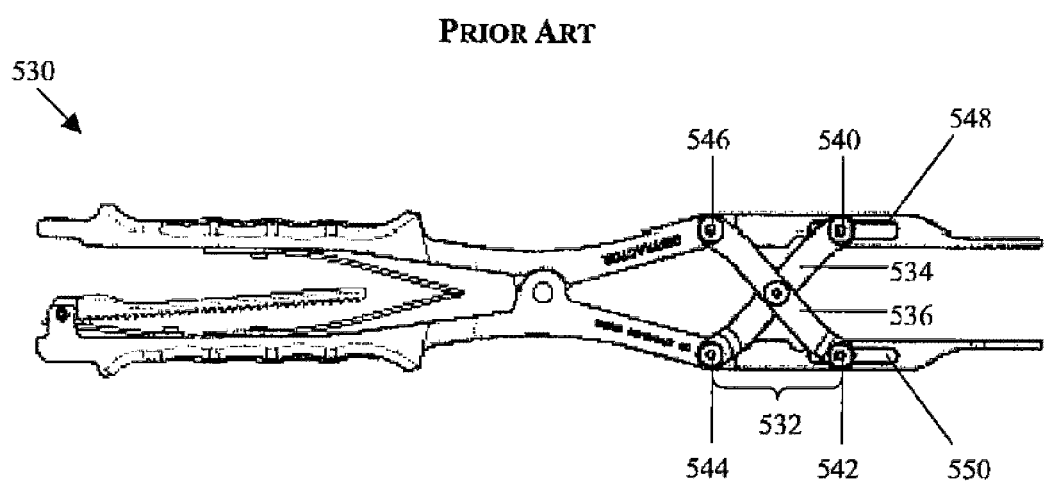
FIG. 5B is a side view of another prior art distraction device that can be used to engage the distraction anchors shown in FIG. 4 to distract the adjacent vertebrae.
Figure 5C:
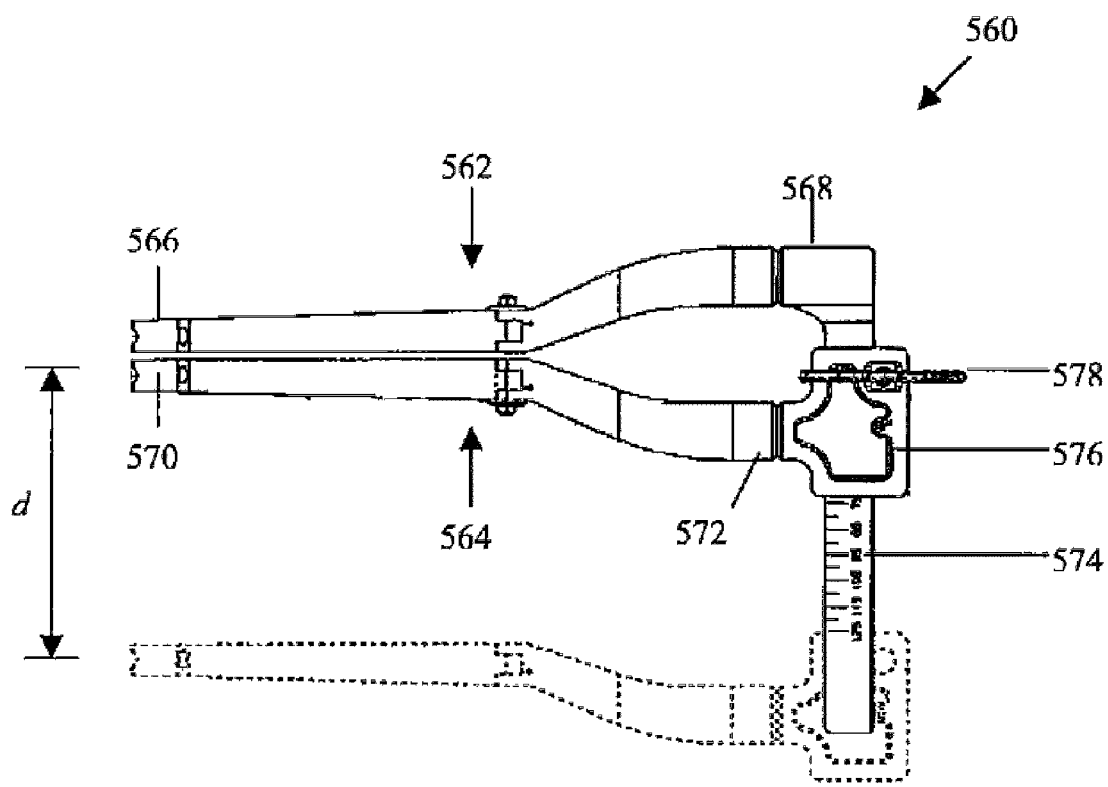
FIG. 5C is a side view of yet another prior art distraction device that can be used to engage the distraction anchors shown in FIG. 4 to distract the adjacent vertebrae.

As previously explained, the present invention generally provides methods for implanting a spinal disc implant and/or a PDS device, such as those previously described, using a posterior surgical approach. FIGS. 4-5C illustrate exemplary methods and devices for distracting adjacent vertebrae using a posterior surgical approach, and FIGS. 6A-9B illustrate exemplary methods and devices for posteriorly introducing a spinal implant into a disc space between adjacent vertebrae. Exemplary methods can also include coupling a PDS device to the adjacent vertebrae, thereby providing a complete motion segment repair system that is implanted using a posterior surgical approach.

Posterior Distraction

FIG. 4 illustrates one exemplary method for distracting two adjacent vertebrae for implanting a disc implant therebetween. In general, the method includes implanting a first pair of distraction anchors (only one anchor 420a is shown) in opposed lateral sides of a first vertebra 430a, and implanting a second pair of distraction anchors (only one anchor 420b is shown) in opposed lateral side of a second vertebra 430b. The distraction anchors can be implanted using techniques known in the art, for example, by drilling holes in the vertebrae for receiving the anchors at the desired implant site. Once the anchors are implanted, they can used to distract the vertebrae to create space for the disc implant. The anchors can also receive bone screws (only two bone screws 410a, 410b are shown) there over to allow a PDS device to be attached to the vertebrae 430a, 430b.

Various devices known in the art can be used to engage the anchors and distract the vertebrae. By way of non-limiting example, FIGS. 5A-5C illustrate exemplary prior art distraction devices. In the embodiment shown in FIG. 5A, the device 500 includes opposed jaws 502a, 502b that have ends 504a, 504b that are configured to engage the distraction anchors. The opposed jaws 502a, 502b are coupled to one another at a pivot point 510, and to first and second arms 508a, 508b which, when moved together, will open the jaws. In use, the opposed jaws 502a, 502b are positioned between the distraction anchors such that the distraction anchors are received within an outer portion of each jaw 502a, 502b. The first and second arms 508a, 508b are then squeezed to open the opposed jaws 502a, 502b to separate the anchors, thereby distracting the vertebrae. The device 500 also includes a ratchet 512 coupled to the arms 508a, 508b for holding the opposed jaws 502a, 502b in an open position, thereby to allowing a disc implant to be inserted between the distracted vertebrae.

FIG. 5B illustrates another embodiment of a distraction device 530 that can be used to distract adjacent vertebrae with distraction anchors implanted on a posterior side of the vertebrae. As shown, the device 530 is similar in configuration to the device 500 shown in FIG. 5A, except that the device 530 of FIG. 5B includes a crossbar assembly 532 for supporting the opposed jaws. The crossbar assembly 532 has first and second bars 534, 536 that are connected to one another by a pivot anchor 538, and that each have first and second ends 540, 542, 544, 546 that mate to the jaws. In particular, the second ends 544, 546 are mated to the jaws at a fixed point, while the first ends 540, 542 are slidably moveable within slots 548, 550 located on the opposed jaws. In use, the opposed jaws are positioned between the distraction anchors and the handle is squeezed to open the opposed jaws to separate the anchors.

FIG. 5C illustrates another embodiment of a prior art distraction device that can be used to distract the anchors shown in FIG. 4. As shown, the device 560 includes a first member that is generally L-shaped with a first arm 562 having first and second 566, 568, and an extension member 574 extending from the second end 568 of the first arm 562. A second arm 564 is slidably coupled to the extension member 574 at a second end thereof 572 by a housing 576, and it extends substantially parallel to the first arm 562 such that a first end 566, 570 of each arm 562, 564 can be used to engage and separate the distraction anchors. The device 500 can also include markings formed on the extension member 574 for indicating a distance d between the first and second arms 562, 564 during distraction, as well as a crank 578 that can be turned to move the second arm 564 along the extension member 574. In use, the first and second ends 566, 570 are coupled to the distraction anchors and the crank 578 is rotated to separate the first and second arms 562, 564, thereby separating the distraction anchors and distracting the adjacent vertebrae to allow for insertion of a disc implant therebetween.

While FIGS. 5A-5C are configured to engage distraction anchors, the devices can be configured to engage one or more bone anchors implanted over the distraction anchors. As previously described, FIG. 4 illustrates cannulated bone screws 410a, 410b that can be guided over the distraction anchors 420a, 420b and threaded into the vertebrae 430a, 430b. Additional bone screws can be implanted over additional distraction anchors implanted on the opposed lateral side (not shown) of the vertebrae. Alternatively, the bone screws or other bone anchors can be implanted over the distraction anchors after distraction and implantation of the disc implant has occurred.

Figure 5E:
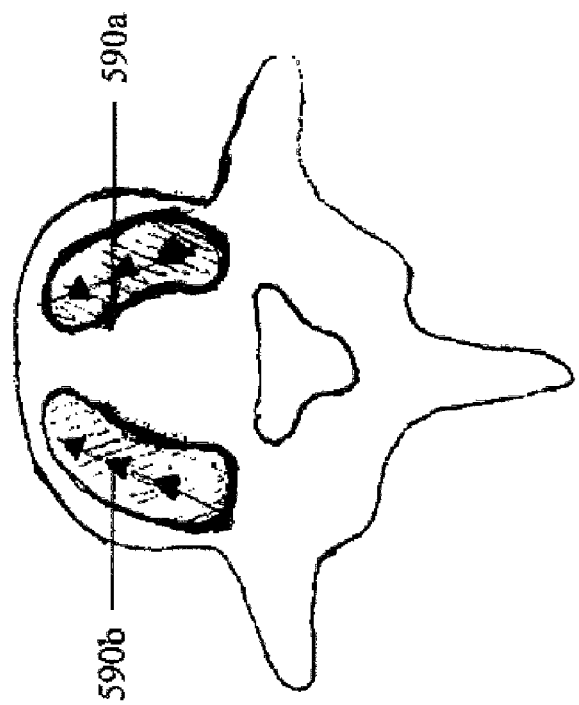
FIG. 5E is a top view of the vertebrae shown in FIG. 5E, showing a second portion of the disc implant implanted on the first side of the disc space.
Figure 5D:
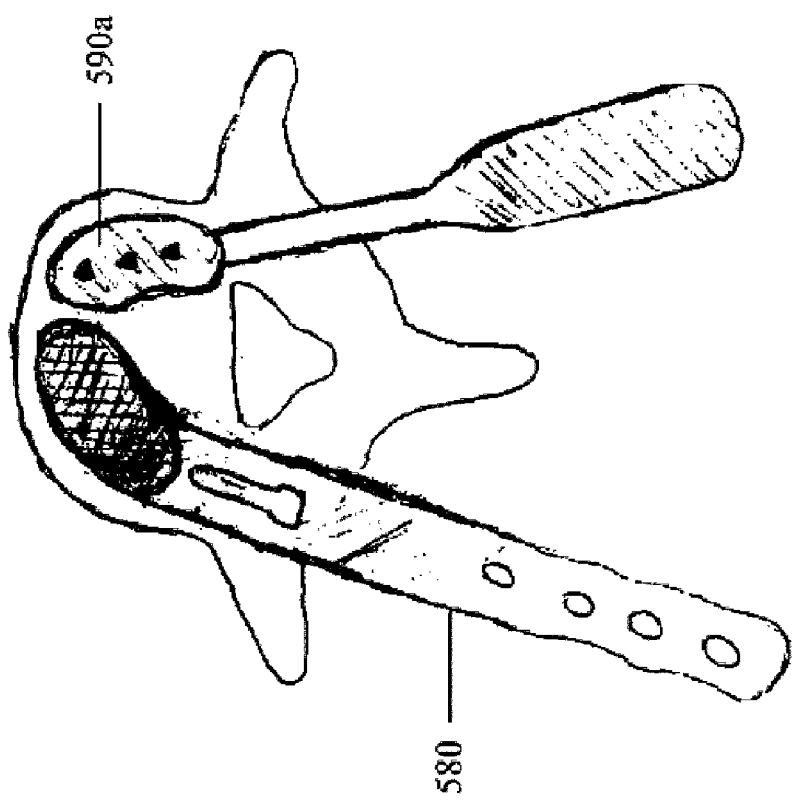
FIG. 5D is top view of one exemplary method for positioning a two-piece disc implant between adjacent vertebrae by distracting a first side of the disc space and implanting a first portion of the disc implant on a second side of the disc space.
Figure 5F:
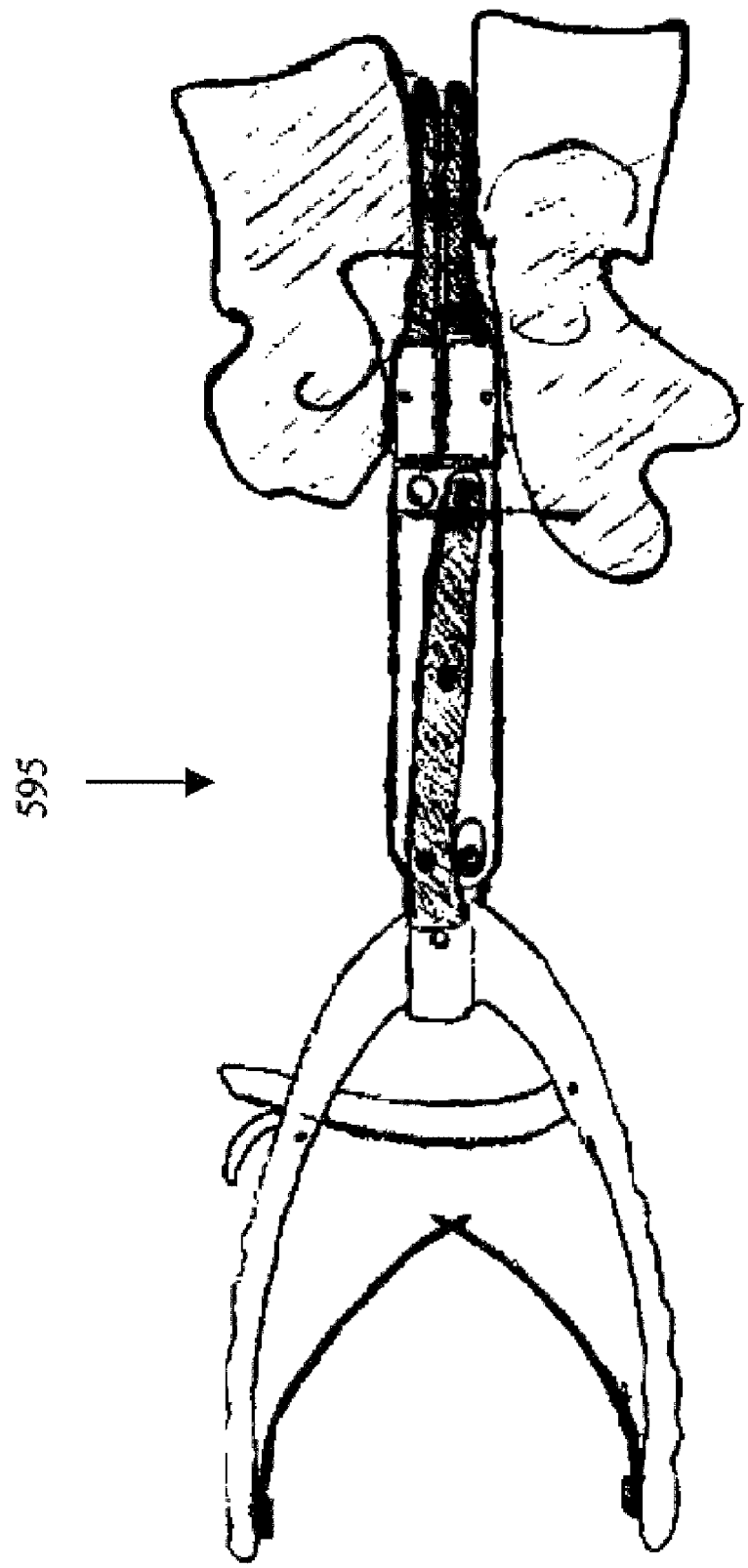
FIG. 5F is a side view of another exemplary embodiment of a distraction device that can be use to facilitate distraction of adjacent vertebrae.

A person skilled in the art will appreciate that a variety of other distraction methods can be used. For example, the bone screws can be used directly for distraction without the use of anchors, or the bone screws and/or anchors can be used as a secondary distraction means to facilitate distraction using other methods and devices. Distraction can also optionally be achieved within the disc space. FIGS. 5D and 5E illustrate one exemplary embodiment of a method for directly distracting a disc space using a multi-piece disc implant. As shown in FIG. 5D, the contralateral side of a disc space is distracted using a distraction tool 580, and a first portion 590a of a disc implant is partially or fully inserted into the ipsilateral side of the disc space. The distractor 580 is then removed, and the second portion 590b of the disc implant, if necessary, is implanted into the contralateral side of the disc space, as shown in FIG. 5E. Where a single piece disc implant is used, the disc implant can be partially inserted on the ipsilateral side when the contralateral side is distracted. The distractor is then removing allowing the disc implant to be fully inserted into its final position between the adjacent vertebrae. As indicated above, the anchors and/or bone screws could optionally be used to aid in distracting the vertebrae. A thin distractor, such as the distractor 595 shown in FIG. 5F, could also optionally be used on the same side of the disc space that the disc implant is being introduced into to aid in insertion and positioning of the disc implant.

Intra-Operative Manipulation of the Spinal Segment

In other embodiments, the anchors and/or bone screws used to couple a PDS device to adjacent vertebrae can be used to facilitate intraoperative manipulation of the spinal segment. For example, the anchors and/or bone screws can be implanted prior to distracting adjacent vertebrae and prior to implanting a disc implant and PDS device, and they can be used to restore normal anatomic alignment, such as the reduction of a listhesis or other deformity or degenerative condition in preparation for implantation of a disc implant. In other embodiments, a temporary rigid device or the PDS device itself could be used to secure the vertebrae in a desired orientation during implantation of a disc implant. For example, a rigid device or the PDS device can be used to maintain the vertebrae in a desired orientation on one side of the vertebrae while implanting at least a portion of the disc implant to be implanted between the disc space on the other side of the vertebrae. The mechanical resistance of the disc implant and/or PCT can also help maintain the restored anatomic alignment, as the disc implant and/or PDS device can be configured to resist anterior shear. This is particularly advantageous for patients with spondylolisthesis.

Posterior Implant Insertion

Various methods and devices are also provided for positioning a disc implant between adjacent vertebrae using a posterior surgical approach. These methods and devices can be used in conjunction with the methods and devices previously described for distracting adjacent vertebrae, or they can be used alone to implant the disc implant and distract the vertebrae simultaneously.

Figure 6A:
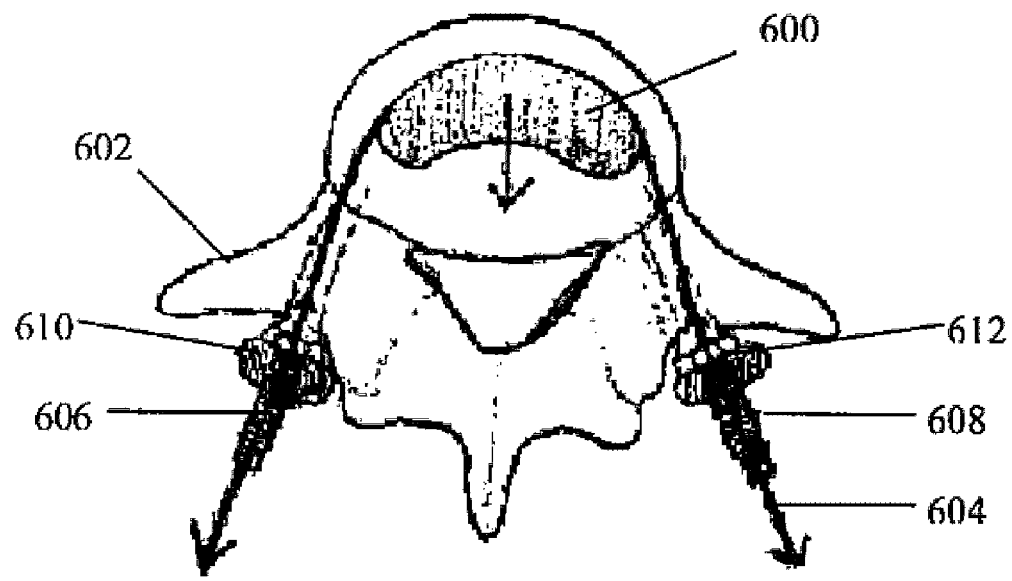
FIG. 6A is a top view of one exemplary embodiment of a method for positioning a disc implant between adjacent vertebrae using a guide wire and two support members coupled to distraction anchors implanted in opposed lateral sides of each vertebrae.

FIGS. 6A-7B illustrate various techniques for introducing a disc implant into a disc space between adjacent vertebrae using a posterior surgical approach. In an exemplary embodiment, as shown in FIG. 6A, a disc implant is positioned on the anterior side of a disc space between adjacent vertebrae using a posterior approach. The implant can then be pulled in a posterior direction using, for guidewire, to position the implant at a desired location between the vertebrae. Pulling the implant in the posterior direction can be effective to further distract the posterior disc space, or alternatively one of the distraction techniques previously described can be used.

Figure 6B:
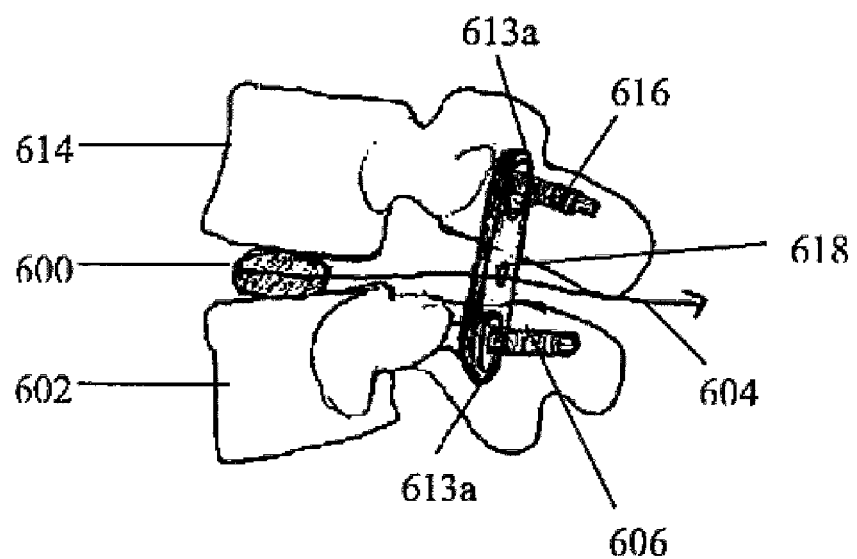
FIG. 6B is a side view of the adjacent vertebrae shown in FIG. 6A, showing the guide wire and one of the support members.

Once the implant is positioned in the anterior portion of the disc space, the implant can be pulled in a posterior direction to position the implant within the disc space. One exemplary technique for moving the disc implant in a posterior direction is shown in FIGS. 6A and 6B. As shown in FIG. 6A, a guidewire 604 is positioned around the anterior side of a disc implant 600 by feeding the guidewire 604 posteriorly between the superior vertebra 614 (shown in FIG. 6B) and the inferior vertebra 602 through a first lateral side and pulling the guidewire out of the opposed lateral side. U.S. patent application Ser. No. 11/055,566 filed on Feb. 10, 2005 and entitled "Intervertebral Prosthetic Disc And Method For Installing Using A Guidewire," illustrates an exemplary technique for positioning a guidewire around a disc implant.

Once the guidewire is positioned around the implant, the opposed ends of the guidewire can be used to pull the implant in the posterior direction. While a pulling force can be applied directly to the guidewire, or a cable tensioning device can be used, in one exemplary embodiment, as shown in FIG. 6A-6B, the distraction anchors are used to redistribute the load necessary to move the implant. In particular, a first support plate 610 can coupled to a first pair of distraction anchors 606, 616 (shown in FIG. 6B) implanted on a first lateral side of the vertebrae, and a second support plate 612 can be coupled to a second pair of distraction anchors (only one distraction anchor 608 is shown in FIG. 6A) implanted in a second lateral side of the vertebrae. Each plate 610, 612 can have a variety of shapes and sizes, but in the illustrated embodiment each plate 610, 612 includes superior and inferior bores (superior and inferior bores 613a, 613b on plate 610 are shown in FIG. 6B) for receiving the distraction anchors 606, 616, and a central bore 618 through which the guidewire 604 can be passed to direct the load along the axis of the distraction anchors. Once the guidewire is passed through the plates 610, 612, the ends of the guidewire 604 can be pulled using, for example, a cable tensioning device, to move the implant 600 in a posterior direction and thereby position the implant between the adjacent vertebrae. Pulling the implant in a posterior direction can also be effective to further distract the posterior disc space, or alternatively, one of the distraction techniques previously described can be used. Distracting the vertebrae using the implant and the support plates allows the load to be directed along the axis of each distraction anchor and eliminates the need to distract using the anchors as distraction can cause the distraction anchors to loosen. While the support plates are described for use with the distraction anchors, the support plates can also be configured to be disposed over the bone screws.

Figure 7A:
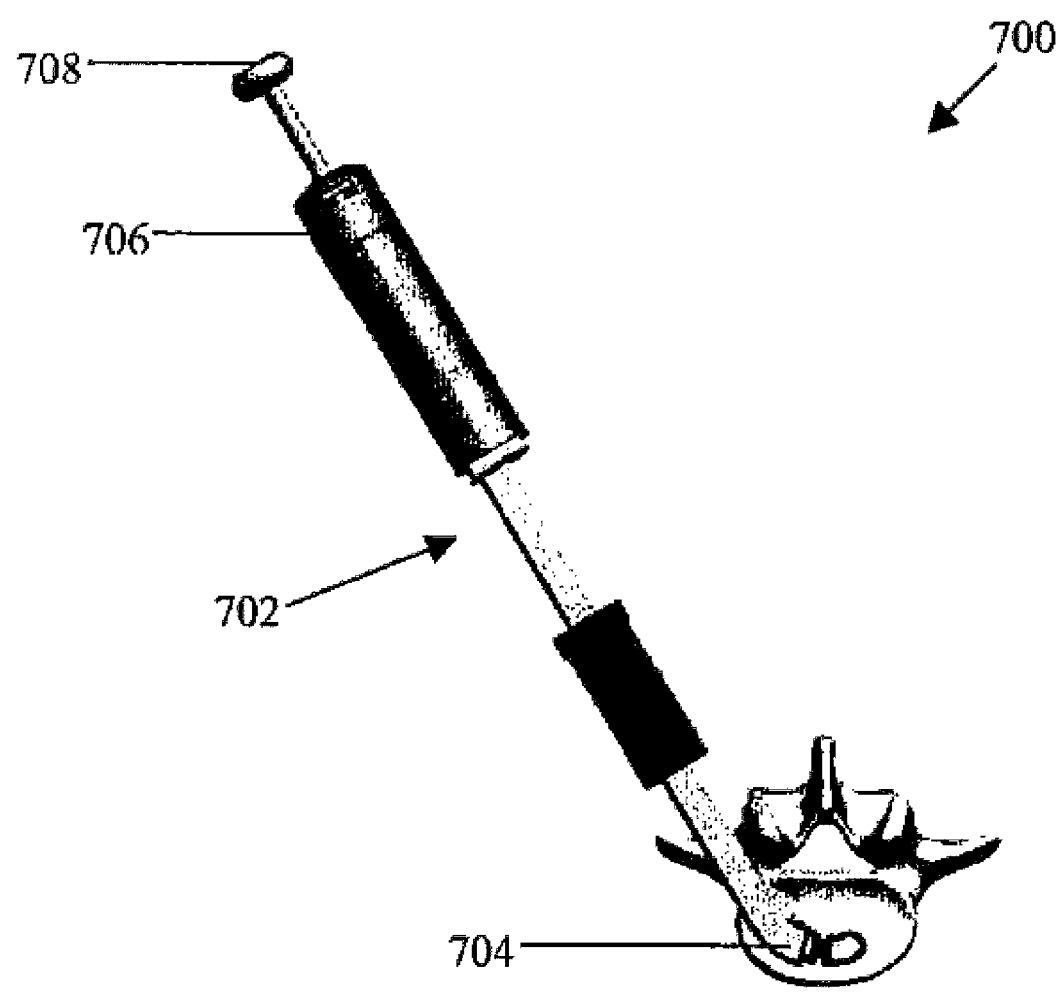
FIG. 7A is a top view of a prior art device that can be used to insert a disc implant into the disc space between adjacent vertebrae.
Figure 7B:
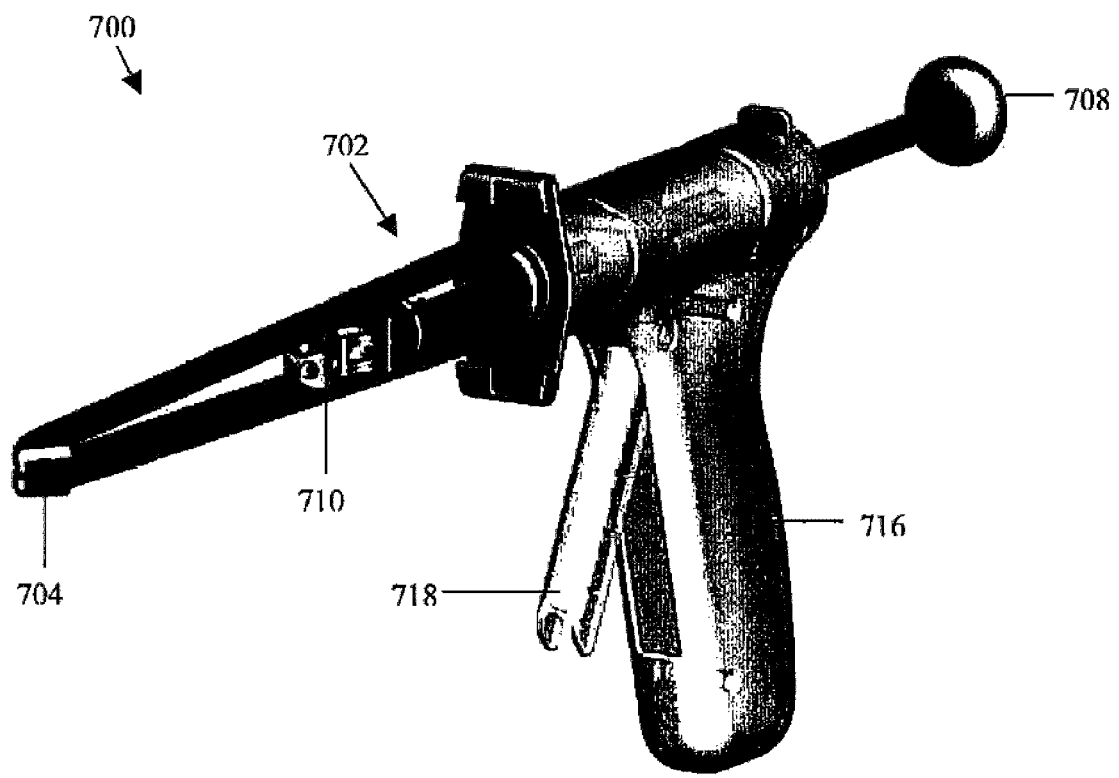
FIG. 7B is a side view of the prior art device shown in FIG. 7A.

A variety of devices can be used to position a disc implant in the disc space using a posterior approach. FIGS. 7A-7B show one embodiment of a guide device that is effective to slide a disc implant 710 (shown in FIG. 7B) into a disc space. As shown, the guide device 700 includes opposed arms 702 that form an elongate pathway therebetween for seating a disc implant 710. The proximal end 704 of the arms 702 can be curved to guide the implant 710 as it is directed along the pathway and into the disc space. The arms of the device may also be used to initiate distraction of the disc space. The device 700 can also include a handle housing 716 to facilitate grasping of the device, and a pusher shaft 708 extending through the handle housing 716 and between the opposed arms 702 for pushing the implant 710 along the pathway and into the disc space. The housing 716 can also include a trigger 718 formed thereon and movably coupled thereto for advancing the pusher shaft 708 between the opposed arms 702 to insert the implant 710 into the disc space. In use, the implant 710 is positioned between the opposed arms 702, and the trigger 718 is squeezed to drive the pusher shaft 708 distally, thereby driving the implant 710 along the pathway. As the implant 710 is guided along the pathway, the curved distal end 704 will cause the implant 710 to pivot so that it can be advanced into the disc space. Further positioning should not be required, but if needed, it may be done using the guide wire technique described previously.

Figure 8:
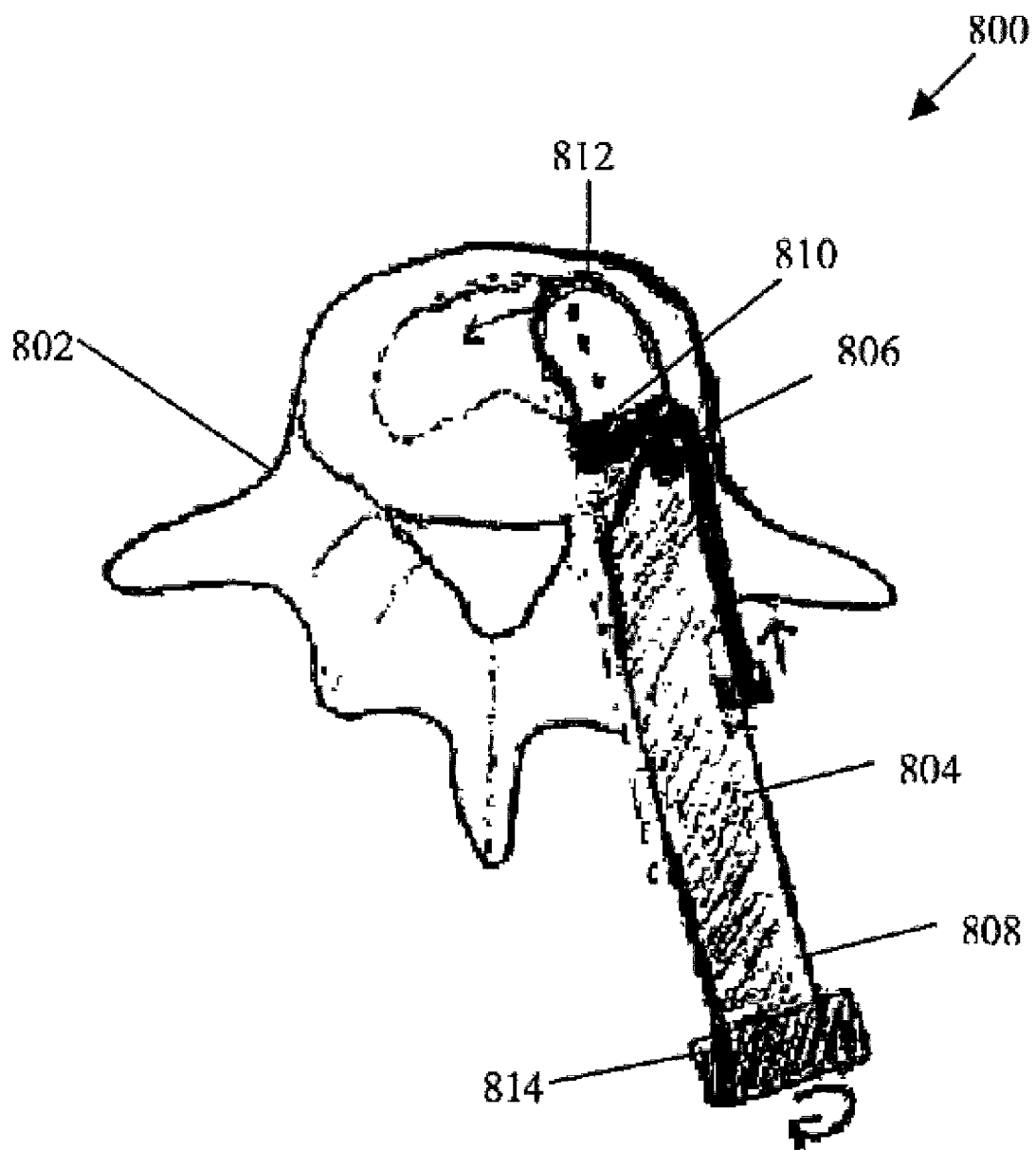
FIG. 8 is a top view of another exemplary embodiment of a method for inserting a disc implant into the disc space between adjacent vertebrae using a guide device having a pivoting member formed thereon for pivoting the disc implant into the disc space.

In another embodiment, shown in FIG. 8, a guide device 800 can be used to position a disc implant in the disc space without the need to pull the implant in a posterior direction. Distraction may be achieved via several methods, but in an exemplary embodiment, distraction is performed in the disc space on the contralateral side. As shown in FIG. 8, the device 800 has a generally elongate shape with a pivoting member 810 formed on a distal end 806 thereof. The pivoting member 810 is configured to engage a disc implant 812 and to pivot the disc implant into position between a superior and inferior vertebrae (only inferior vertebra 802 is shown). A variety of techniques can be used to engage the implant including, for example, a threaded member, a dovetail connection, opposed arms, etc. The device can also include an actuation mechanism 814 formed on a proximal end 808 thereof for actuating the pivoting member 810, and a release mechanism (not shown) to release the implant from the pivoting member 810. In the illustrated embodiment, the device 800 includes a rotatable actuation mechanism 814 that is coupled to a gear assembly disposed within the distal portion of the elongate shaft and effect to pivot the implant. In use, the distal end 806 is inserted into the disc space between the superior and inferior vertebrae using a posterior approach. The turning mechanism 814 is rotated to pivot the implant 812 into position between the superior and inferior vertebrae, and then the release mechanism releases the implant into the disc space.

PDS Device Placement

Various methods and devices are also provided for coupling a PDS device (ranging from a dynamic stabilizer to a complete facet replacement) to adjacent vertebrae using a posterior surgical approach. After the disc implant is inserted into the disc space between two adjacent vertebrae and positioned using the exemplary methods and devices described above, a PDS device can be attached to the vertebrae using bone anchors to provide a full motion segment repair system. As previously mentioned, at least one of the PDS device and the disc implant can have a floating center of rotation to allow the PDS device to be implanted at various locations relative to the vertebrae. However, it may be necessary to measure a depth of the disc implant within the disc space to facilitate selection and/or positioning of the PDS device.

Figure 9A:
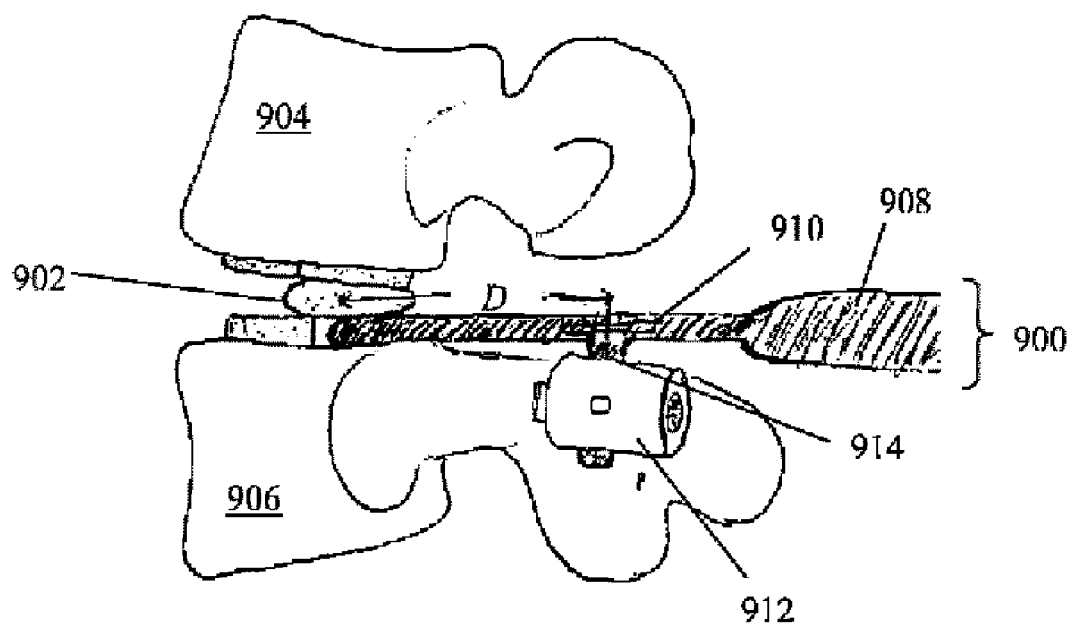
FIG. 9A is a side view of a depth gauge indicator for determining proper placement of a posterior stabilization device based on a depth of a disc implant disposed between superior and inferior vertebrae.
Figure 9B:
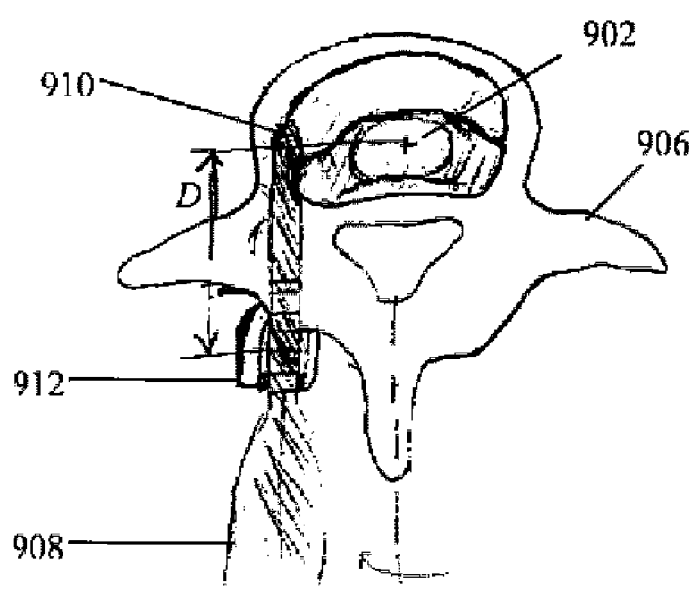
FIG. 9B is a top view of the device shown in FIG. 9A.

Accordingly, FIGS. 9A-9B illustrate one embodiment of a depth gauge indicator 900 that can be used to determine proper size and/or placement of a PDS device based on a depth of a disc implant 902 disposed between superior and inferior vertebrae 904, 906. As shown, the indicator 900 includes has a generally elongate shaft with a distal end is adapted to be inserted between the adjacent vertebrae to the location of the disc implant, and a proximal portion with markings 910 formed thereon. The device can also include a handle 908 to facilitate grasping. As is further shown, the device includes an extension member 914 that is slidably coupled to the proximal portion and that is adapted to be received within the head of a bone anchor 912. The position of the extension member 914 relative to the markings 910 can indicate the depth D of the implant 902. This depth can then be used to select a PDS device having the appropriate size and/or to position the PDS device.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for implanting a motion segment repair system, comprising:
   implanting a disc implant in a disc space between adjacent superior and inferior vertebrae using a substantially posterior surgical approach and positioning the disc implant on an anterior side of the disc space;
   positioning a guidewire around the implant such that opposed terminal ends of the guidewire extend through a support member extending between a posterior surface of the adjacent superior and inferior vertebrae;
   pulling opposed terminal ends of the guidewire such that a mid-portion of the guidewire positioned around an anterior portion of the disc implant moves the implant in a posterior direction in the disc space;
   removing the support member; and coupling a posterior stabilization device to the adjacent superior and inferior vertebrae.

2. The method of claim 1, wherein at least one of the disc implant and the posterior stabilization device has a floating center of rotation to allow the posterior stabilization device to be positioned at various locations relative to the adjacent superior and inferior vertebrae.

3. The method of claim 2, wherein the disc implant has a floating center of rotation.

4. The method of claim 3, wherein implanting the disc implant comprises implanting first and second end plates with a central core moveably disposed therebetween between the adjacent superior and inferior vertebrae.

5. The method of claim 2, wherein the posterior stabilization device has a floating center of rotation.

6. The method of claim 5, wherein coupling the posterior stabilization device to adjacent superior and inferior vertebrae comprises coupling a first connector of the posterior stabilization device to the superior vertebra and coupling a second connector of the posterior stabilization device to the adjacent inferior vertebrae, the first and second connectors being movably mated to one another by a flexible member to allow motion between the adjacent superior and inferior vertebrae.

7. The method of claim 2, wherein the posterior stabilization device has a floating center of rotation.

8. The method of claim 2, wherein the posterior stabilization device has a fixed center of rotation.

9. The method of claim 8, wherein coupling the posterior stabilization device to adjacent superior and inferior vertebrae comprises coupling a first connector of the posterior stabilization device to the superior vertebra and coupling a second connector of the posterior stabilization device to the adjacent inferior vertebrae, the first and second connectors being slidably coupled to one another to allow at least some flexion and extension between the adjacent superior and inferior vertebrae.

10. The method of claim 2, wherein the floating center of rotation is adapted to allow at least some flexion, extension, lateral bending, and axial rotation between the adjacent superior and inferior vertebrae.

11. The method of claim 1, wherein implanting the disc implant comprises distracting the adjacent superior and inferior vertebrae using one or more distraction anchors disposed in a posterior side of the adjacent superior and inferior vertebrae.

12. The method of claim 1, further comprising, prior to coupling a posterior stabilization device, measuring a distance between the disc implant and at least one anchoring element implanted in a posterior surface of the adjacent superior and inferior vertebrae, and using the measured distance to select a posterior stabilization device having an appropriate size.

13. A method for implanting a motion segment repair system, comprising:
  distracting adjacent superior and inferior vertebrae using a spreading device that engages at least one distraction anchor disposed in a posterior side of each of the adjacent superior and inferior vertebrae;
  inserting a disc implant between the adjacent superior and inferior vertebrae;
  pulling on first and second ends of a guidewire having a mid-portion positioned around the implant such that the mid-portion of the guidewire moves the implant in a posterior direction, the guidewire extending through a support member extending between the distraction anchors;
  removing the support member;
  implanting a bone screw over each distraction anchor; and
  coupling a posterior stabilization device to the bone screws to couple the adjacent superior and inferior vertebrae to one another.

14. The method of claim 13, wherein first and second distraction anchors are implanted on opposed lateral sides of the superior vertebra, and third and fourth distraction anchors are implanted on opposed lateral sides of the inferior vertebra.

15. The method of claim 13, wherein the disc implant is inserted using a substantially posterior surgical approach.

16. A method for implanting a motion segment repair system, comprising:
  introducing a disc implant to an anterior location between adjacent superior and inferior vertebrae using a substantially posterior surgical approach;
  positioning a guidewire around the disc implant such that opposed first and second ends of the guidewire extend through a support member extending between a posterior surface of the adjacent superior and inferior vertebrae;
  pulling the first and second ends of the guidewire such that a mid-portion of the guidewire positioned around an anterior portion of the disc implant moves the disc implant in a posterior direction to position the disc implant between the adjacent superior and inferior vertebrae;
  removing the support member; and
  coupling a posterior stabilization device to the adjacent superior and inferior vertebrae.

17. The method of claim 16, wherein pulling the disc implant in a posterior direction is effective to distract the adjacent superior and inferior vertebrae.

18. The method of claim 16, wherein the disc implant is introduced between the adjacent superior and inferior vertebrae using a guide device.

19. A method for implanting a motion segment repair system, comprising:
  introducing a disc implant between adjacent superior and inferior vertebrae;
  implanting one or more distraction anchors in the adjacent superior and inferior vertebrae;
  applying tension to a member coupled to the disc implant to move the disc implant in a posterior direction, the tension being applied such that a support member extending between the superior and inferior vertebrae and having the member extending therethrough redistributes a load along an axis of the one or more distraction anchors.

20. The method of claim 19, wherein the support member extends between the distraction anchors.

21. The method of claim 20, wherein the member comprises a guidewire extending around the disc implant, and the support member has first and second bores for receiving opposed ends of the guidewire

* * * * *